United States Patent [19]
Hamajima et al.

[11] Patent Number: 5,807,363
[45] Date of Patent: Sep. 15, 1998

[54] ABSORBENT ARTICLE

[75] Inventors: Mitsugu Hamajima; Yasuo Toyoshima; Hironori Kawasaki; Yayoi Fukuhara; Minoru Nakanishi, all of Tochigi-ken, Japan

[73] Assignee: Kao Corporation, Tokyo, Japan

[21] Appl. No.: 704,944

[22] Filed: Aug. 30, 1996

[30] Foreign Application Priority Data

Sep. 12, 1995 [JP] Japan ................................. 7-233858

[51] Int. Cl.⁶ .................................................. A61F 13/15
[52] U.S. Cl. ........................... 604/366; 604/378; 604/387
[58] Field of Search .................................... 604/365, 366, 604/368, 378–387

[56] References Cited

U.S. PATENT DOCUMENTS

| | | | |
|---|---|---|---|
| 3,967,623 | 7/1976 | Butterworth et al. | 604/383 |
| 4,496,359 | 1/1985 | Pigneul | 604/387 |
| 5,211,641 | 5/1993 | Roos et al. | 604/385 |
| 5,391,162 | 2/1995 | Widlund et al. | 604/387 |
| 5,613,960 | 3/1997 | Mizutani | 604/380 |

FOREIGN PATENT DOCUMENTS

| | | | |
|---|---|---|---|
| 0520884 | 12/1992 | European Pat. Off. | 604/379 |
| 0554565 | 8/1993 | European Pat. Off. | 604/378 |
| 63-20820 | 2/1988 | Japan . | |
| 9310733 | 6/1993 | WIPO | 604/385.2 |

*Primary Examiner*—John G. Weiss
*Assistant Examiner*—K. M. Reichle
*Attorney, Agent, or Firm*—Birch, Stewart, Kolasch & Birch, LLP

[57] ABSTRACT

An absorbent article has a substantially elongated shape and includes a topsheet 2, a backsheet 3, and an absorbent member 4. The topsheet 2 includes a sheet member which has one surface 2a exhibiting hydrophobic properties and another surface 2b exhibiting hydrophilic properties. The one surface of the topsheet is a skin contactable surface, and the other surface faces the absorbent member 4. The backsheet serves as an anti-leakage sheet and is disposed at opposing longitudinal side portions of an upper surface of the absorbent article inwardly from side edges 1a of the absorbent member so that the backsheet forms a pair of hydrophobic areas A. Each of the hydrophobic areas A has a continuous or discontinuous sealed portion 10 formed by sealing the topsheet 2 and the backsheet 3 along each inner edge A' of each hydrophobic areas A. A body fluid retaining portion 20 is provided at a location lying outside of the sealed portion 10 on the skin contactable surface of the absorbent article. The body fluid retaining portion 10 is formed by folding the topsheet 2 so that the hydrophilic surface 2b forms the inside of the fold.

7 Claims, 7 Drawing Sheets

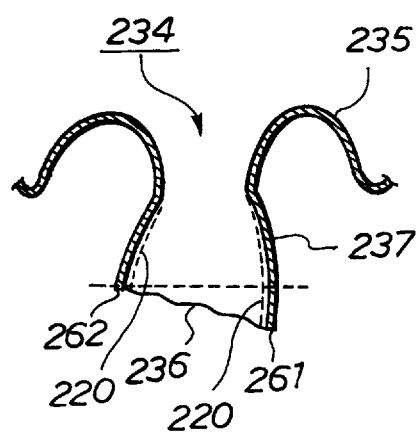
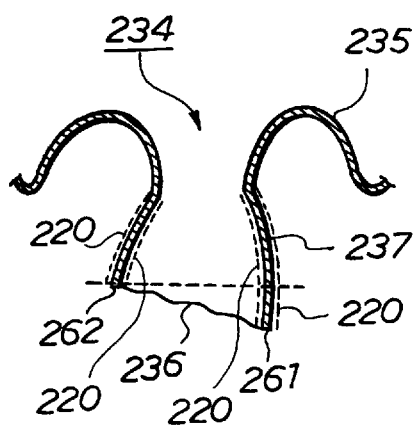
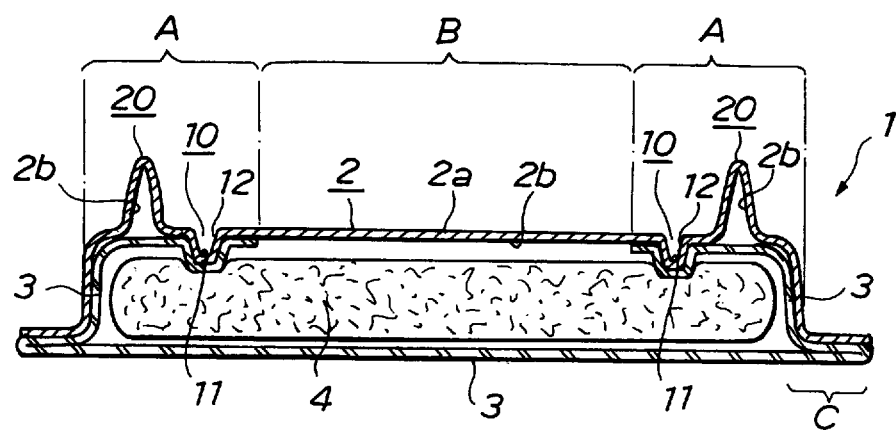

ABSORBENT ARTICLE

BACKGROUND OF THE INVENTION

1. Field of the Invention

This invention relates to an absorbent article such as a sanitary napkin or an incontinent pad, and more particularly to an absorbent article which exhibits excellent antileakage properties and also provides an excellent feeling during use.

2. Description of the Related Art

An absorbent article such as a sanitary napkin usually comprises a liquid permeable topsheet, a liquid impermeable backsheet, and a liquid retentive absorbent member interposed between the topsheet and the backsheet. The absorbent article typically has an elongated shape. Such an absorbent article has the problems that discharged body fluids (a) are not absorbed and flow on to the surface to the surface of the topsheet or the body fluids (b) ooze into the topsheet sideways with respect to the absorbent article, or the body fluids (c) once absorbed ooze to the topsheet of the absorbent article and ooze sideways, causing liquid leakage from the side portions.

In view of the above problems, Japanese Utility Model Application Laid-Open 63-20820 proposes an absorbent article, such as a sanitary napkin, in which an antileakage sheet is wound up (or rolled up) on an upper surface of the absorbent article to form hydrophobic areas at both opposing longitudinal side portions of the absorbent article. The topsheet and the antileakage sheet are sealed to provide a sealed portion in the hydrophobic area, so that the problem of oozing liquid on the topsheet is improved.

However, heretofore even the above-described absorbent article cannot sufficiently solve the liquid oozing/liquid leakage problems with respect to the topsheet.

That is, where the surface of the topsheet has hydrophilic properties, the amount of the side leakage caused by the surface flow onto the surface of the topsheet becomes small because the discharged body fluids are absorbed rapidly from the topsheet. However, imparting hydrophobic properties to the topsheet cannot be realized sufficiently because the topsheet has hydrophilic properties. Consequently, oozing liquid cannot be sufficiently suppressed. Further, where liquid flows over the sealed portion and oozes to the outside of the sealed portion, the degree of oozing becomes great enough to cause side leakage because the topsheet has hydrophilic properties. Thus, the problem of liquid oozing into the topsheet sideways with respect to the absorbent article and that of liquid oozing to the topsheet of the absorbent article and outwardly sideways caused by liquid returned from the absorbent article are not yet fully obviated.

Further, when the topsheet has hydrophobic properties, and the sealed portion is imparted sufficient hydrophobic properties, liquid oozing in the topsheet can be suppressed. However, when the topsheet has hydrophobic properties, there is a problem that the rate of absorbing body fluids becomes small and therefore the body fluids cannot be absorbed and flow over the sealed portion. Further, there is another problem in that the body fluids flowing over the sealed portion and to the outside cannot be retained because the topsheet has hydrophobic properties. The liquid leakage is also likely to occur due to the movement of the wearer.

SUMMARY OF THE INVENTION

It is therefore an object of the present invention to provide an absorbent article which more effectively suppresses liquid leakage, such as surface flow, liquid oozing in the topsheet, and liquid oozing in the topsheet caused by the liquid returned from the absorbent member, so as to prevent liquid leakage from the side portions of the absorbent article, thus providing excellent antileakage performance.

As a result of careful search and hard study for obviating the above problems, it has been found that the above object can be achieved by an absorbent article which has a body fluid retaining portion provided at a location lying along the outside of the sealed portion and also on the skin contact surface side of the absorbent article.

The present invention has been accomplished on the basis of the above finding. The present invention provides a substantially elongated absorbent article comprising: a liquid permeable topsheet, a liquid impermeable backsheet, and a liquid retentive absorbent member interposed between the topsheet and the backsheet, wherein the topsheet comprises a sheet member which has one surface exhibiting hydrophobic properties and another surface exhibiting hydrophilic properties, the one surface being a skin contactable surface of the absorbent article, and the other surface facing the absorbent member;

the absorbent article further comprising an antileakage sheet disposed at opposing longitudinal side portions of an upper surface of the absorbent article inwardly from side edges of the absorbent article so that the antileakage sheet forms a pair of hydrophobic areas each having an inner edge;

each of the hydrophobic areas having a sealed portion formed by sealing the topsheet and the antileakage sheet continuously or discontinuously along its inner edge; and a body fluid retaining portion provided at a location laterally outwardly of each sealed portion on the skin contactable surface of the absorbent article, the body fluid retaining portion being formed by a fold in the topsheet so that after the fold is formed, an interior surface of the fold is defined by the other surface of the topsheet exhibiting hydrophilic properties.

The present invention also provides an absorbent article, wherein the topsheet comprises a sheet member having a plurality of perforations.

The present invention also provides an absorbent article, wherein the sealed portion forms an antileakage groove.

The present invention also provides an absorbent member, wherein the antileakage sheet comprises the backsheet or another antileakage sheet.

The present invention also provides an absorbent article, wherein the depth of each antileakage groove 0.3 to 12 mm.

The present invention also provides an absorbent article, wherein the width of each hydrophobic area is 3 to 30 mm, and the width of a liquid absorbing area located between the pair of hydrophobic areas is 30 to 70 mm.

The present invention also provides an absorbent article, wherein the distance from its inner side edge of each hydrophobic area to the antileakage groove is 1 to 20 mm.

The absorbent article of the present invention more effectively suppresses liquid leakage, such as surface flow, liquid oozing in the topsheet, and liquid oozing in the topsheet caused by liquid returned from the absorbent member, so as to prevent liquid leakage from the side portions of the absorbent article, thus providing excellent antileakage performance.

BRIEF DESCRIPTION OF THE DRAWINGS

FIGS. 6A and 6B are partly enlarged sectional views each showing an example of a manner of applying a surface active agent to the sheet member shown in FIGS. 5A through 5C.

FIG. 7 is a width-wise sectional view (corresponding to FIG. 2) showing another embodiment of a sanitary napkin serving as the absorbent article of the present invention;

DETAILED DESCRIPTION OF THE EMBODIMENT

The present invention will now be described in more detail with reference to the drawings.

Figure 1:
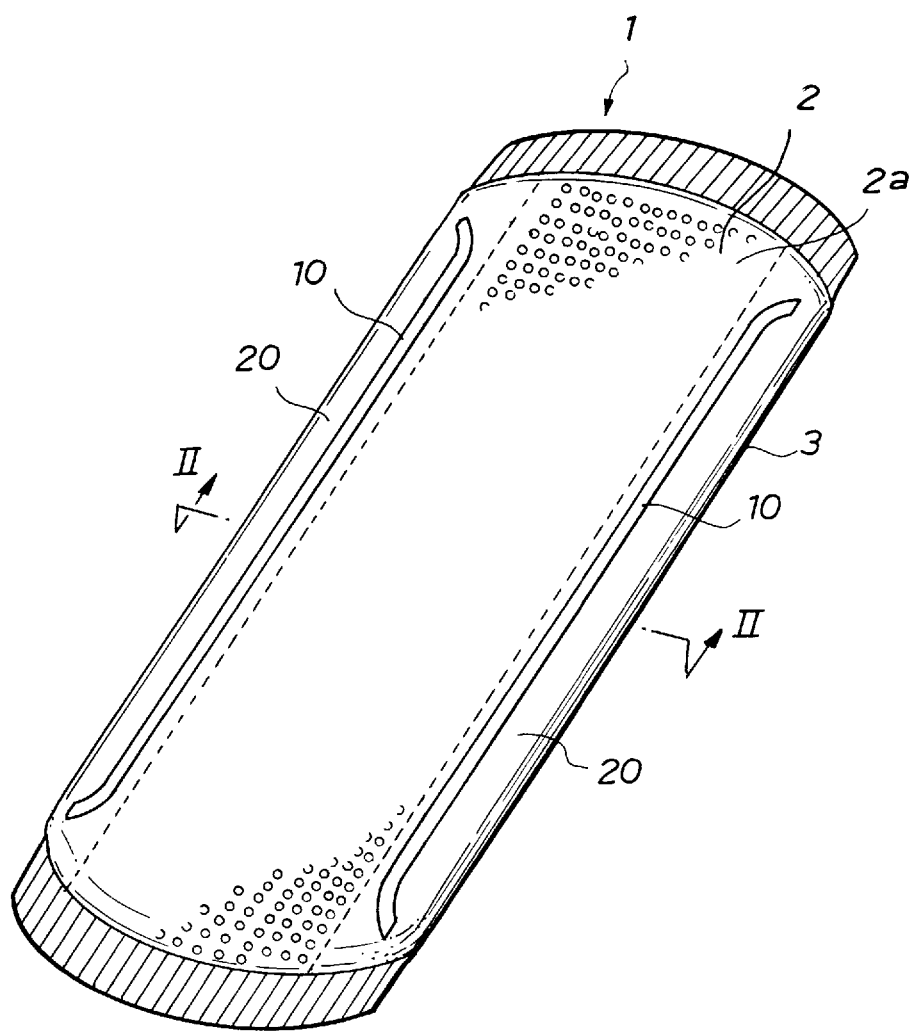
FIG. 1 is a perspective view showing an embodiment of a sanitary napkin serving as an absorbent article of the present invention.
Figure 2:
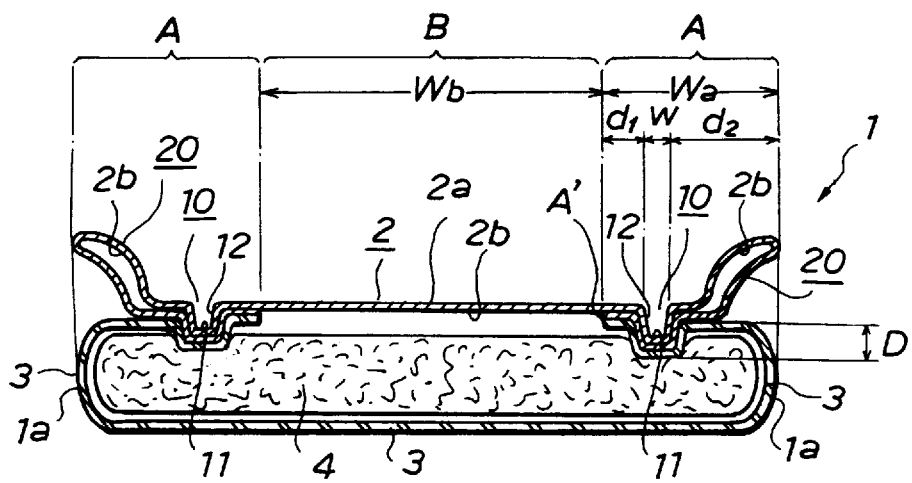
FIG. 2 is a sectional view taken on line II—II of the sanitary napkin of FIG. 1.

FIG. 1 is a perspective view showing an embodiment of a sanitary napkin serving as an absorbent article of the present invention, and FIG. 2 is a sectional view taken on line II—II of the sanitary napkin of FIG. 1.

The sanitary napkin 1 of this embodiment serving as an absorbent article shown in FIGS. 1 and 2 comprises a liquid permeable topsheet 2, a liquid impermeable backsheet 3, and an absorbent member 4 (see FIG. 2) interposed between the topsheet 2 and the backsheet 3, having a substantially elongated shape, as per known sanitary napkins.

More specifically, as shown in FIGS. 1 and 2, in the sanitary napkin 1, the topsheet 2 is disposed on an upper surface of an absorbent member 4 and the backsheet 3 is disposed on a lower surface of the absorbent member 4.

On the lower surface of the backsheet 3, an adhesive is applied to form a slipping-off preventing portion (not shown).

In the sanitary napkin 1 of this embodiment, the topsheet 2 is formed of the above-mentioned sheet member. The topsheet 2 is disposed such that the one surface 2a is located on the skin contact surface (upper surface) side of the sanitary napkin, and the other surface 2b is located on the absorbent member 4 side. The backsheet 3 serving as an antileakage sheet is disposed at opposing longitudinal side portions of the upper surface of the sanitary napkin 1 inwardly (towards a liquid absorbing area B side as later described) from the side edge 1a. A pair of hydrophobic areas A are formed by the backsheet 3. Each of the hydrophobic areas A has a continuous sealed portion 10 formed by sealing the topsheet 2, the backsheet 3 and the upper surface side of the absorbent member 4 along each inner edge A' of the hydrophobic areas A. A body fluid retaining portion 20 is provided at a location lying outside of the sealed portion 10 and also on the upper surface side of the sanitary napkin 1, the body fluid retaining portion 20 being formed by bending the topsheet 2 so that the other surface 2b comes inside.

More specifically, the hydrophobic areas A are formed by covering the side surfaces of the absorbent member 4 and the side edge portions of the upper surface side of the absorbent member 4 with the backsheet 3 which is disposed on the lower surface side of the absorbent member 4. A liquid absorbing area B is formed between the pair of hydrophobic areas A.

The sealed portions 10 are formed by heat sealing the hydrophobic areas A in the longitudinal direction of the sanitary napkin 1. As shown in FIG. 2, the sealed portions 10 serve as antileakage grooves. Each groove includes a bottom surface portion 11, and a peripheral wall portion 12 adjoining the bottom surface portion 11.

Each body fluid retaining portion 20 is formed into a bag bending the side edge portions of the topsheet 2 sidewardly and sealing the same. In so doing, the bent side edge portions of the topsheet 2 together with an adjacent portion of the topsheet exposed at the upper surface forms the sealed portion 10 and defines a hollow tubular member extending in the longitudinal direction of the sanitary napkin 1. Since the inner surface of the body fluid retaining portion 20 is the other surface 2b exhibiting hydrophilic properties, the small amount of body fluids which may flow on the surface over the antileakage grooves can be absorbed and retained by the body fluid retaining portion 20.

The peripheral length of the topsheet 2 forming the bag-like body fluid retaining portion 20 (i.e., the peripheral length of the body fluid retaining portion 20) is preferably to 5 to 50 mm, more preferably 10 to 30 mm. If the peripheral length is shorter than 5 mm, the amount of body fluids which ooze over the sealed portion retained in the retaining portion 20 is unfavorably reduced. If the peripheral length is longer than 50 mm, the portion 20 may cause an unusual feeling, or the retaining portion 20 may unfavorably project outside the opposing longitudinal side edges of the sanitary napkin to degrade the feel of the napkin.

The width W of each antileakage groove serving as the sealed portion 10 is preferably 0.1 to 20 mm, more preferably 0.1 to 10 mm. If the width W of the sealed portion is smaller than 0.1 mm, suppression of body fluid oozing, at the sealed portion, becomes unfavorably weak. If the width W is larger than 20 mm, it may become uncomfortable and degrade the feel of the napkin.

The depth D of each antileakage groove is preferably 0.3 to 12 mm, more preferably from 0.3 to 3 mm. A preferred range is 0.5 to 2 mm. If the depth is smaller than 0.3 mm, suppression of body fluid oozing at the antileakage groove becomes unfavorably low. If the depth is larger than 12 mm, it becomes uncomfortable and degrades the feel of the napkin.

The width Wa of the hydrophobic area A is preferably 3 to 30 mm, and the width Wb of the liquid absorbing area B located between the pair of hydrophobic areas A is preferably 30 to 70 mm. If the width Wa is smaller than 3 mm, the area for forming the sealed portion and the liquid retaining portion becomes too small, so that antileakage performance decreases. If the width Wb is larger than 30 mm, the absorbing surface becomes so small that it may become uncomfortable and degrade the feel of the napkin. Also, if the width Wb of the absorbing area is smaller than 30 mm, the absorbing surface becomes so small that leakage is likely to occur. If the width Wb is larger than 70 mm, the width of a resultant product itself becomes so large that it tends to become uncomfortable to the wearer.

The distance d1 from the inner side edge A' of the hydrophobic area A to the antileakage groove 10 is preferably 1 to 20 mm, whereas the distance d2 from the outer side edge (side edge of the sanitary napkin) of the hydrophobic area A to the antileakage groove 10 is preferably 1 to 20 mm.

If the distance d1 is smaller than 1 mm, the distance between the absorbing surface and the antileakage groove becomes so small that the effect of suppression of body fluid oozing is reduced. If the distance d1 is larger than 20 mm, the hydrophobic area A becomes too broad because the hydrophobic area A has the antileakage groove 10 and the body fluid retaining portion 20 as well.

The material of each member of the sanitary napkin will now be described.

The material constituting the topsheet 2 is a sheet member which has one surface 2a exhibiting hydrophobic properties and the other surface 2b exhibiting hydrophilic properties. In this embodiment, a sheet member having a plurality of perforations is employed.

More specifically, the one surface 2a can be formed preferably by using a hydrophobic film which does not become wet even after absorbing body fluids and which is made of, for example, a polyolefin selected from the group consisting of polyethylene, polypropylene, copolymers thereof, and the like.

The term "hydrophobic" used herein means that liquid does not spread on the one surface and the surface has a contact angle of above 90 degrees. The term "contact angle" refers to an angle of a water drop formed between a water/air interface and a water/the one surface interface at a normal connection point of these two interfaces. Every above-mentioned polyolefin has a contact angle of larger than 90 degrees, and therefore the one surface exhibits hydrophobic properties. For example, polyethylene has a contact angle of 94 degrees, and polypropylene has a contact angle of 95 degrees. ["Hyomen" by Shimeo Gotoh, 27, 689 (1989)].

The term "hydrophilic" means that the other surface by itself causes liquid to spread, that is, it has a contact angle of less than 90 degrees. In order that the one surface may absorb body fluids as fast as possible, the other surface preferably has a contact angle of 30 degrees or less.

The other surface can be formed preferably by using a hydrophilic material such as polyvinyl alcohol, rayon and pulp, or a material which has been rendered hydrophilic by applying or internally lining a surface active agent to an upper surface of a polyolefin such as polyethylene and polypropylene so as to reduce the contact angle of the surface.

The surface active agent is not particularly limited as long as the agent can reduce the contact angle to 90 degrees or less, preferably 30 degrees or less, when applied to the surface thereof. Non-limiting examples of the surface active agent include, for example, nonionic surface active agents, anionic surface active agents, cationic surface active agents, and amphoionic surface active agents. Specific examples of these surface active agents are mentioned, for example, in "Shin-ban Kaimen Kasseizai Handobukku (second edition, issued by Kogaku Tosho Kabushiki Kaisha, Jan. 20, 1991) pp. 13 to 36".

Among them, the nonionic surface active agent and anionic surface active agent excel in properties other than wet properties, for example, in heat resisting properties, light resisting properties, anti-oxygen properties, and anti-organic solvency properties. A single surface active agent or a mixture of two or more surface active agents is selected from them according to the required performances.

Preferred examples of the surface active agent include HLB 3 to 20 nonionic surface active agents, such as C8 to C18 alkyl glucoside, sorbitan esters of fatty acids (C8 to C18), polyoxyethylene sorbitan esters of fatty acids (C8 to C18), esters of polyoxyethylene fatty acids (C8 to C18); and anionic surface active agents, such as alkali metal salts and amine salts of C8 to C24 alkyl phosphate esters, alkali metal salts of alkyl sulfate, alkali metal salt of alkyl, alkyl benzene or alkyl naphthalene sulfonate, alkali metal salts of polyoxyethylene alkyl ether sulfate, and alkali metal salts of alkyl sulfo-succinate. These surface active agents can be used individually or in combination.

Figure 3:
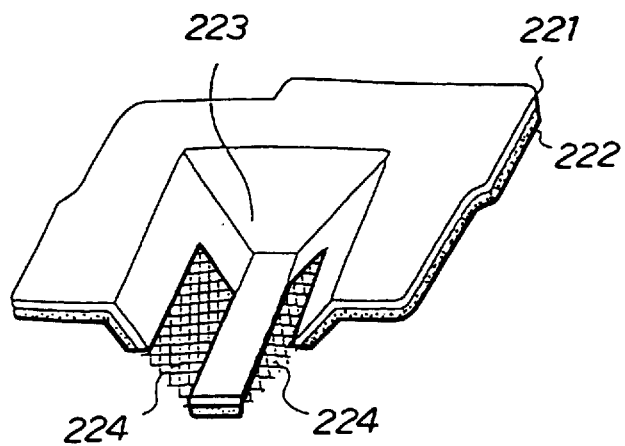
FIG. 3 is a partly enlarged schematic view showing one example of a sheet member which is preferably used as a topsheet in the present invention.

As a preferred example of the sheet member used in the present invention, a sheet member as shown in FIG. 3 is mentioned. The sheet member of FIG. 3 has a skin contact surface side formed of a hydrophobic film 221 of a polyolefin series, and a skin non-contact surface side formed of a non-woven fabric 222 made of paper or a synthetic resin which has been rendered hydrophilic with a surface active agent. The sheet member is obtained by laminating the hydrophobic film 221 and the non-woven fabric 222 to form a unitary sheet, and applying perforation processing to the resulting sheet, so as to form a recess 223 having a plurality of perforations 224, thereby to provide a sheet member having a plurality of perforations.

As another preferred example of the sheet member, a perforated film formed by perforating a polyolefin film (i.e., a sheet member having a plurality of perforations) can be employed. More specifically, the perforated film has one surface exhibiting hydrophobic properties and the other surface exhibiting hydrophilic properties, and can be obtained by selectively applying a surface active agent only to the back surface side of a perforated film having a through-hole structure. The through-hole structure has a plurality of hole portions which include a plurality of adjacent apex portions formed of a convexly curved surface having a void back side, a perforated bottom portion, and a sleeve-like wall portion for connecting them. The perforated bottom portion defines each of the perforations for allowing the passage of liquid therethrough.

As a method of applying the surface active agent, any known methods can be employed. The surface active agent can be applied selectively to the back surface side by a spray coating, a gravure coating, or the like.

Figure 4A:
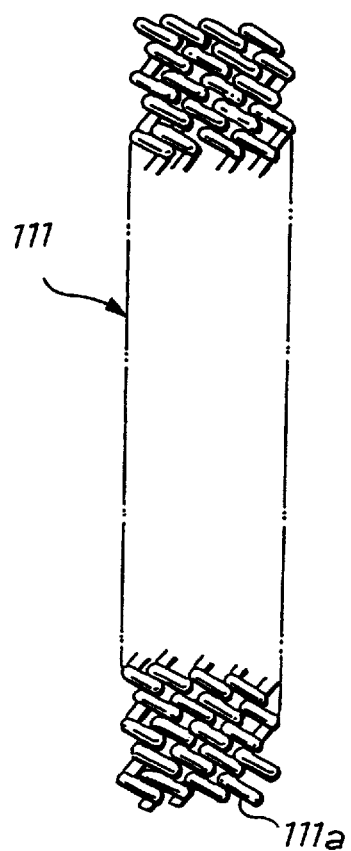
FIGS. 4A and 4B are schematic views showing a metal net to be used when a sheet member is manufactured which sheet member is preferably used as the topsheet in the present invention.
Figure 4B:
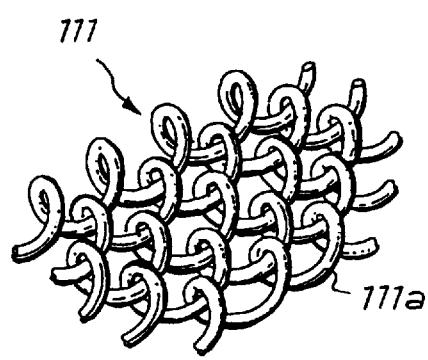

The perforated film of this type can be obtained, as described in Japanese Patent Application Laid-Open 7-184957 which is incorporated herein by reference, by subjecting a melt resin composed of the above-mentioned polyolefin to hot air treatment with a same-oriented spirally-woven metal net 111 having clockwise or counterclockwise windings as shown in FIGS. 4A and 4B, so that a sheet having a configuration in accordance with the surface configuration of the metal net 111 and also having hole portions at the locations corresponding to the spaces formed among wires 111a of the spirally-woven metal net 111 is formed.

Figure 5A:
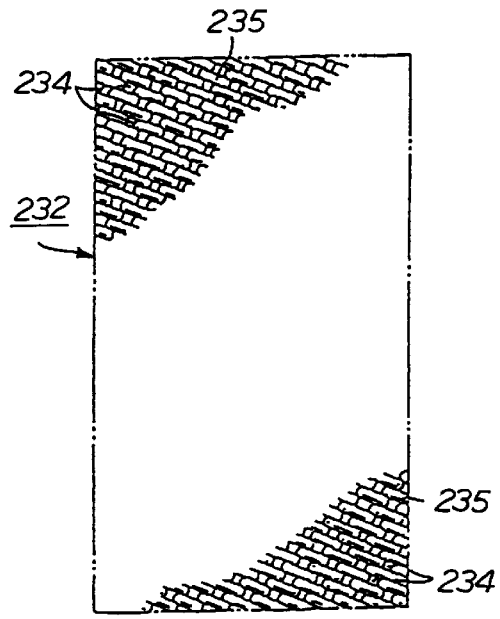
FIG. 5A is a schematic view showing another embodiment of the sheet member which is preferably used as the topsheet in the present invention.
Figure 5B:
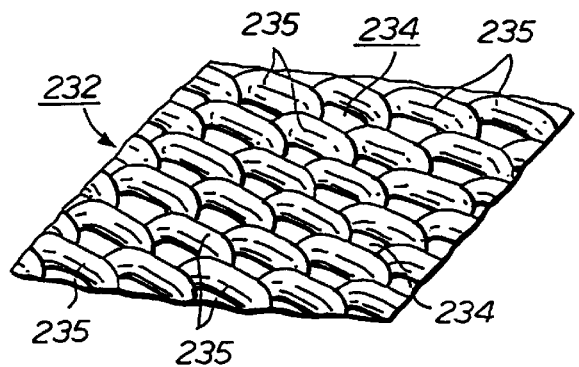
FIG. 5B is an enlarged view of FIG. 5A.
Figure 5C:
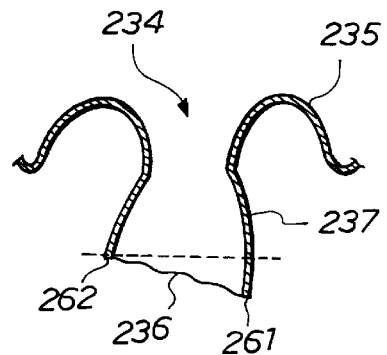
FIG. 5C is an enlarged sectional view of FIG. 5A.

The sheet member composed of the perforated film will now be described specifically with reference to FIGS. 5 and 6. As shown in FIGS. 5A through 5C, the sheet member 232 composed of the above-mentioned perforated film has a plurality of hole portions 234 surrounded by a plurality of apex portions 235 each including a convexly curved surface having a void back side. Each of the hole portions 234 includes a plurality of adjacent apex portions 235, a perforated bottom portion 236, and a sleeve-like wall portion 237 with a lower peripheral edge 261 and upper peripheral edge 262 for connecting them. A perforation for allowing the passage of liquid therethrough is defined by the perforated bottom portion 236. As shown in FIGS. 6A and 6B, a surface active agent 220 is applied to the other surface side so that the other surface side is rendered hydrophilic. As shown in FIGS. 6A and 6B, the surface active agent 220 may be applied to either a single surface or both surfaces of the film.

Alternatively, another preferred example of non-woven fabric which has one surface exhibiting hydrophilic properties and the other surface exhibiting hydrophobic properties is obtained by overlaying together a non-woven fabric which is composed of a hydrophilic material such as polyvinyl alcohol, rayon and pulp, or of fibers which have been rendered hydrophilic by applying or internally lining a surface active agent to the surface of a polyolefin, such as polyethylene and polypropylene, to reduce the contact angle of the surface, and a non-woven fabric which has a hydrophobic surface composed of polypropylene, polyethylene, or polyethylene/polypropylene or polyethylene/polyester composite fibers, or a hydrophobic non-woven fabric which have been subjected to oil treatment by using a hydrophobic oil agent of a silicon or fluorine series; and forming the overlaid non-woven fabrics into a unitary body by, for example, thermal fusing, embossing or hot melting.

No limitation is imposed on the composition of the backsheet 3 as long as the surface has hydrophobic properties and the backsheet 3 does not permeate liquid. Preferred examples of the backsheet include a laminated non-woven fabric obtained by laminating a non-woven fabric having a hydrophobic surface and polyethylene, and a liquid-preventive film made of a polyolefin series such as polyethylene. Features which are not particularly described, for example, the material of the absorbent member 4, can be constructed in the same manner as in conventionally known absorbent articles.

Since the sanitary napkin 1 of this embodiment has the sealed portion 10 in the hydrophobic area A, liquid, once absorbed, does not ooze out again on the surface to cause surface liquid flow. Also, even where liquid flows over the sealed portion 10 and flows onto the surface, flowed-over liquid is absorbed and retained by the body fluid retaining portion 20 so that liquid leakage from the side portions, caused by the surface liquid flow, does not occur.

Where the sealed portion 10 forms the antileakage groove as in this embodiment, prevention of liquid from oozing out is significantly large. Moreover, since the body fluid can be guided to the body fluid retaining portion 20, prevention of surface liquid flow of the body fluids at the body fluid retaining portion 20 can be enhanced.

Further, in the sanitary napkin 1 of this embodiment, the upper surface on the skin contact surface side has hydrophobic properties and the lower surface has hydrophilic properties, and the top sheet 2 has an ideal hydrophobic/hydrophilic gradient from the skin contact surface side towards the absorbent member side. With this configuration, body fluids can be smoothly absorbed by the absorbent member 4 without causing surface liquid flow. Furthermore, since the sanitary napkin 1 has the sealed portion 10 in the hydrophobic area A, the napkin 1 effectively prevents side leakage caused by body fluids oozing through the topsheet or body fluids returning from the topsheet. Also, even when the body fluids go over the sealed portion 10, these body fluids are absorbed and retained by the body fluid retaining portion 20. Therefore, body fluids which flow on the upper surface of the topsheet and flow over the sealed portion, and body fluids which ooze through the topsheet and flow over the sealed portion can be retained by the liquid retaining portion 20. Accordingly, the amount of body fluids leaking from the side portions is markedly reduced, and therefore side leakage can be prevented more effectively.

The sanitary napkin 1 of this embodiment can be easily prepared by winding the backsheet up towards the upper surface side of the absorbent member; bringing the surface (the one surface) of a folded part of the topsheet, which is folded such that the other surface serves as the inner surface, into contact with the backsheet located in the hydrophobic area and bonding thereto; sealing and compressing the hydrophobic area by a heated emboss roll or the like; and forming the antileakage groove as the sealed portion.

Other embodiments of the absorbent article of the present invention will now be described with reference to FIGS. 7 through 9.

Figure 8:
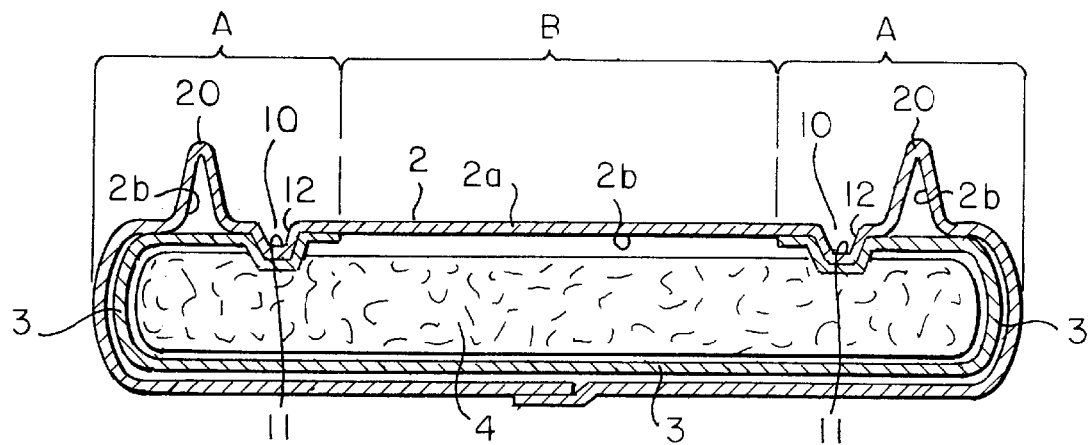
FIG. 8 is a width-wise sectional view (corresponding to FIG. 2) showing still another embodiment of a sanitary napkin serving as the absorbent article of the present invention.
Figure 9:
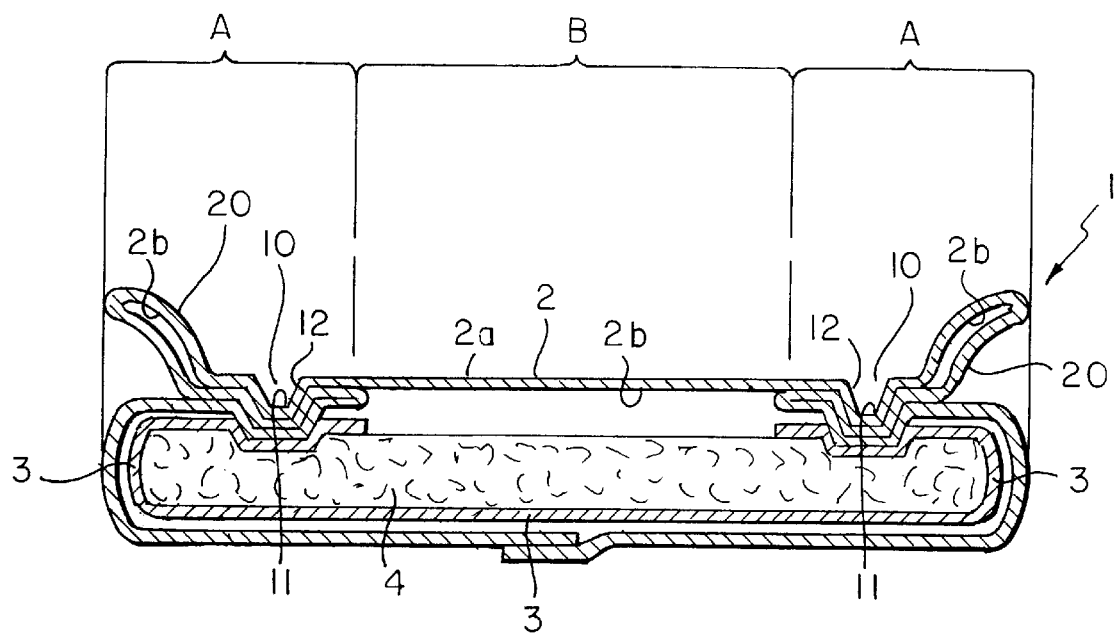
FIG. 9 is a width-wise sectional view (corresponding to FIG. 2) showing still another embodiment of a sanitary napkin serving as the absorbent article of the present invention.

FIG. 7 is a width-wise sectional view (corresponding to FIG. 2) showing another embodiment of a sanitary napkin as the absorbent article of the present invention, FIG. 8 is a width-wise sectional view (corresponding to FIG. 2) showing a further embodiment of a sanitary napkin as the absorbent article of the present invention, and FIG. 9 is a width-wise sectional view (corresponding to FIG. 2) showing a still further embodiment of a sanitary napkin as the absorbent article of the present invention.

In the descriptions of the sanitary napkins of the following embodiments, the features different from those in the sanitary napkin of the embodiment shown in FIGS. 1 and 2 are particularly described. With respect to the features which are not particularly referred to, the descriptions on the sanitary napkin shown in FIGS. 1 and 2 apply appropriately.

In the sanitary napkin 1 of the embodiment shown in FIG. 7, the backsheet 3 serving as an antileakage sheet is extended outwardly from the side edge of the absorbent member on the lower surface side of the sanitary napkin, and bent towards the absorbent member 4 side to cover the side surface of the absorbent member 4 and the side portion of the upper surface. The topsheet 2 covers the upper surface of the absorbent member 4 and opposite side surfaces of the absorbent member 4. The topsheet 2 extends outwardly from the side edge of the absorbent member 4 on the lower surface side of the sanitary napkin 1. This extended portion is bonded to the bent backsheet 3 to form a side flap portion C.

The body fluid retaining portion 20 is formed by folding the topsheet 2 so as to form a chevron shape on the upper surface side of the sanitary napkin 1 and provides, as a whole, a hollow projection extending in the longitudinal direction.

Figure 10:
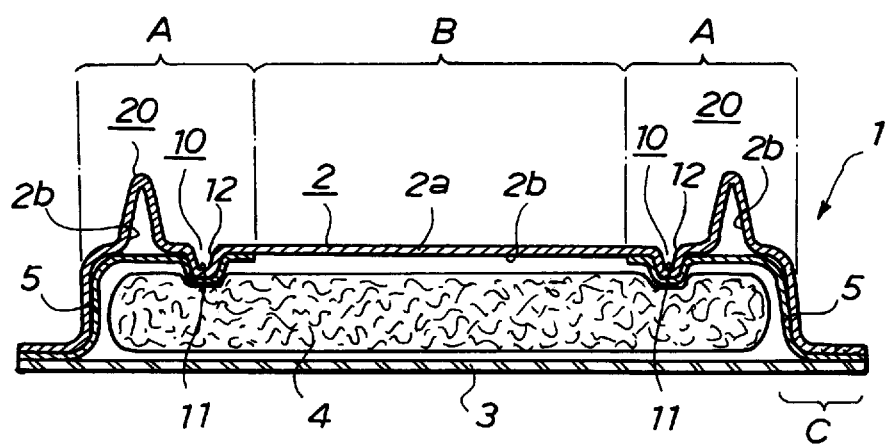
FIG. 10 is a width-wise sectional view (corresponding to FIG. 2) showing yet another embodiment of a sanitary napkin serving as the absorbent article of the present invention.

In this embodiment, the body fluid retaining portion 20 may be formed in the same configuration (manner) as in the embodiment shown in FIGS. 1 and 2, i.e., in the form of a hollow tubular member. Also, in this embodiment, as shown in FIG. 10, instead of folding the backsheet 3, an antileakage sheet 5 other than the backsheet 3 may be provided so as to form the hydrophobic areas A (in this case, the side flap portion C is constituted by the topsheet 2, the backsheet 3, and the antileakage sheet 5 interposed therebetween). In this case, for the antileakage sheet other than the backsheet, any antileakage sheet used for conventional napkins can be employed without any particular limitation. The antileakage sheet may be made of the same material as that of the backsheet.

In the sanitary napkin 1 of the embodiment shown in FIG. 8, the topsheet 2 covers the upper surface and opposite side surfaces of the absorbent member 4; and opposing side edges are overlapped with each other and bonded together generally at the center on the lower surface side of the sanitary napkin 1. The backsheet 3 serving as an antileakage sheet covers the lower surface and side surfaces of the absorbent member 4, and the opposing longitudinal side portions of the upper surface at a location between the absorbent member 4 and the topsheet 2, thereby to form the hydrophobic area A.

The body fluid retaining portion 20 is formed by folding the topsheet 2 in such a manner as to form a chevron shape on the upper surface side of the sanitary napkin 1 and provides, as a whole, a hollow projection extending in the longitudinal direction.

In the sanitary napkin 1 of the embodiment shown in FIG. 9, the topsheet 2 is folded back at the outer side edge on the upper surface side of the sanitary napkin and then further folded back towards the outer side edge to cover the upper surface and opposite side surfaces of the absorbent member 4. Then, opposing side edges are overlapped with each other and bonded together generally at the center of the lower surface side of the sanitary napkin 1. The backsheet 3 serving as an antileakage sheet covers the lower surface and side surfaces of the absorbent member 4, and also the opposing side portions of the upper surface, thereby to form the hydrophobic area A at a location between the absorbent member 4 and the topsheet 2.

The body fluid retaining portion 20 is formed by folding back the topsheet 2 at the outer side edge on the upper surface side of the sanitary napkin 1, and provides, as a whole, a hollow bag shape extending in the longitudinal direction.

Owing to the above-mentioned construction, the depth of the antileakage groove serving as the sealed portion 10 can be increased.

The sanitary napkins of the embodiments shown in FIGS. 7 through 9 can exhibit the same effect as the sanitary napkin of the embodiment shown in FIGS. 1 and 2.

The absorbent article of the present invention is not limited to the above embodiments and various modifications can be made without departing from the scope of the subject matter of the present invention.

For example, in the above embodiments, the sealed portion 10 is continuously formed, but the present invention is not limited thereto. It may be arranged such that a plurality of sealed portions having a tetragonal shape, such as a rectangular shape, a circular shape, or the like are arranged in the longitudinal direction of the absorbent article to provide discontinuous antileakage grooves serving as the sealed portion.

The sealed portion 10 may be merely heat sealed and does not need to form an antileakage groove. Also, the sealed portion may be formed by any method other than heat sealing, for example, by a method of using an adhesive. The sealed portion 10 may be formed simply by bonding the topsheet and the backsheet together.

The hydrophobic area may be formed by arranging an antileakage sheet other than the backsheet in place of the backsheet. For the antileakage sheet, any antileakage sheet used for conventional sanitary napkins may be employed without any limitation.

As the fixing member of the absorbent article, wing portions may be provided on opposing side edge portions in place of or in addition to the above-mentioned slipping-off preventing agent.

As the topsheet 2, in place of the perforated film (i.e., a sheet member having a plurality of perforations), a nonwoven fabric of a multilayered structure obtainable by bonding a hydrophobic non-woven fabric and a hydrophilic non-woven fabric together may be employed.

What is claimed is:

1. A substantially elongated absorbent article comprising a liquid permeable topsheet, a liquid impermeable backsheet, and a liquid retentive absorbent member interposed between said topsheet and said backsheet:

wherein said topsheet comprises a sheet member which has one surface exhibiting hydrophobic properties and another surface exhibiting hydrophilic properties, said one surface being a skin contactable surface of said absorbent article, and said other surface facing said absorbent member;

said absorbent article further comprising an antileakage sheet disposed at opposing longitudinal side portions of an upper surface of said absorbent article inwardly from side edges of said absorbent article so that said antileakage sheet forms a pair of hydrophobic areas each having an inner edge;

each of said hydrophobic areas having a sealed portion formed by sealing said topsheet and said antileakage sheet continuously or discontinuously along its inner edge; and a body fluid retaining portion provided at a location laterally outwardly of each to said sealed portion on said skin contactable surface of said absorbent article, said body fluid retaining portion being formed by a fold in said topsheet so that after said fold is formed, an interior surface of said fold is defined by said other surface of said topsheet exhibiting hydrophilic properties.

2. The absorbent article according to claim 1, wherein said topsheet comprises a sheet member having a plurality of perforations.

3. The absorbent article according to claim 1, wherein said sealed portion forms an antileakage groove.

4. The absorbent article according to claim 1, wherein said antileakage sheet comprises said backsheet or another antileakage sheet.

5. The absorbent article according to claim 3, wherein the depth of each antileakage groove is 0.3 to 12 mm.

6. The absorbent article according to claim 1, wherein the width of each of said pair of hydrophobic areas is 3 to 30 mm, and the width of a liquid absorbing area located between said pair of hydrophobic areas is 30 to 70 mm.

7. The absorbent article according to claim 3, wherein the distance from the inner edge of each hydrophobic area to said antileakage groove is 1 to 20 mm.

* * * * *